United States Patent
Hettrick et al.

(10) Patent No.: US 7,233,821 B2
(45) Date of Patent: Jun. 19, 2007

(54) METHOD AND APPARATUS FOR EVALUATING VENTRICULAR PERFORMANCE DURING ISOVOLUMIC CONTRACTION

(75) Inventors: Douglas A. Hettrick, Blaine, MN (US); David E. Euler, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 11/097,706

(22) Filed: Mar. 31, 2005

(65) Prior Publication Data

US 2006/0224203 A1 Oct. 5, 2006

(51) Int. Cl.
*A61B 5/02* (2006.01)
*A61B 5/04* (2006.01)
*A61N 1/00* (2006.01)

(52) U.S. Cl. ............. 600/510; 600/508; 600/509; 607/9; 607/14; 607/119

(58) Field of Classification Search ........ 600/508–510, 600/520; 607/9, 14, 119
See application file for complete search history.

(56) References Cited

U.S. PATENT DOCUMENTS

| 6,540,699 B1* | 4/2003 | Smith .................. 600/587 |
| 6,795,732 B2* | 9/2004 | Stadler et al. ............ 607/17 |
| 2004/0015081 A1* | 1/2004 | Kramer et al. ........... 600/439 |

\* cited by examiner

*Primary Examiner*—Robert E. Pezzuto
*Assistant Examiner*—Natasha Patel
(74) *Attorney, Agent, or Firm*—Daniel G. Chapik; Girma Wolde-Michael

(57) ABSTRACT

A method of evaluating ventricular performance of a heart employing sensors to measure a ventricular dimension signal and deriving indices of ventricular performance therefrom. Premature Shortening (PS) and Isovolumic Lengthening (IL) comprise two indices of ventricular performance determined from analysis of the left ventricular dimension signal during the transition from ventricular filling to ventricular ejection. Measured values of PS and IL are compared to other measured values or reference values to determine if ventricular performance has improved (or worsened). In some embodiments, the dimension sensors may comprise piezoelectric sonomicrometer crystals that operate as ultrasound transmitters and receivers. The sensors may be mounted in relation to a ventricle of the heart either temporarily or permanently, and may be configured either separately from or integrally with cardiac pacing leads.

20 Claims, 15 Drawing Sheets

METHOD AND APPARATUS FOR EVALUATING VENTRICULAR PERFORMANCE DURING ISOVOLUMIC CONTRACTION

FIELD OF THE INVENTION

Embodiments of the invention relate generally to implantable medical devices (IMDS) that deliver therapies to the heart and/or monitor cardiac physiologic parameters. More particularly, embodiments of the invention relate to the use of sensors positioned in relation to the heart to monitor physical dimensions of the heart and to collect, derive and utilize information regarding cardiac performance for therapeutic and diagnostic purposes.

BACKGROUND OF THE INVENTION

A wide variety of IMDs have been developed over the years or are proposed that provide cardiac rhythm management of disease states manifested by cardiac rhythm disorders and heart failure. Implantable pacemakers have been developed that monitor and restore heart rate and rhythm of patients that suffer bradycardia (too-slow or irregular heart rate), tachycardia (regular but excessive heart rate), and heart failure (the inability of the heart to maintain its workload of pumping blood to the body). Implantable cardioverter-defibrillators (ICDs) have been developed that deliver programmed cardioversion/defibrillation shocks to the atria, in response to detection of atrial fibrillation (rapid, uncontrolled heartbeats in the atria), or to the ventricles, in response to life-threatening, ventricular tachyarrhythmias. Typically, single and dual chamber bradycardia pacing systems are also incorporated into ICDs.

Cardiac IMDs have traditionally employed the ability to detect or sense electrical activity in the heart as the basis for determining and delivering appropriate therapy. For example, appropriately placed electrical sensors may sense the contractions of the atria and/or the ventricles as evidenced by P-waves and R-waves detected in atrial and ventricular electrogram (EGM) signals, respectively. The timing of detected atrial and ventricular contractions (sensed events) may be used by the IMD to monitor for and treat cardiac arrhythmias such as bradycardia, tachycardia, and fibrillation.

Among the earliest cardiac rhythm management IMDs were single-chamber, fixed-rate pacing systems comprising an implantable pulse generator (IPG) and a lead bearing one or more pace/sense electrodes adapted to be placed in contact with the heart chamber to be paced. These IMDs, commonly referred to as pacemakers, provided fixed-rate pacing to a single heart chamber when the heart rate fell below a programmable lower rate limit.

Another cardiac rhythm management IMD, the implantable cardioverter defibrillator ("ICD"), was developed for treating abnormally fast heart rhythms. The earliest ICDs delivered a defibrillation shock to the ventricles when heart rate, as determined by sensed ventricular contractions, and certain other criteria were met. It was proposed that blood pressure sensors or accelerometers be incorporated in ICDs so that the absence of mechanical heart function during fibrillation could also be detected to confirm the presence of fibrillation before a shock therapy was delivered.

Over the years, pacemakers and ICDs have evolved in complexity and capabilities. Increasingly complex signal processing algorithms have been developed to evaluate electrogram (EGM) signals and to thereby attempt to provide the most appropriate therapy to restore a normal heart rhythm and to avoid delivery of inappropriate therapy that may be painful and potentially harmful to the patient.

It has been recognized that other indicators of heart function, particularly indicators related to mechanical heart function, would be of great value in augmenting the algorithms that process atrial and ventricular EGM signals in order to resolve ambiguities that may arise. It is desirable, for example, to know whether a delivered pacing pulse has "captured" the heart, i.e., caused the heart chamber to contract. Similarly, it is desirable to rapidly determine whether a delivered cardioversion/defibrillation shock has effectively terminated a tachyarrhythmia and whether the heart has returned to a normal rhythm.

There are other situations where it would be useful to incorporate measurements or indications of mechanical heart function in pacing systems. For example, patients suffering from chronic heart failure or congestive heart failure (CHF) often manifest an elevation of left ventricular end-diastolic pressure. This may occur while left ventricular end-diastolic volume remains normal due to a decrease in left ventricular compliance. CHF due to chronic hypertension, ischemia, infarct or idiopathic cardiomyopathy may be associated with compromised systolic and diastolic function involving decreased atrial and ventricular muscle compliance. These conditions may be associated with chronic disease processes, or complications from cardiac surgery with or without specific disease processes. Most heart failure patients suffer from conditions which may include a general weakening of the contractile function of the cardiac muscle, attendant enlargement thereof, impaired myocardial relaxation, and depressed ventricular filling characteristics in the diastolic phase following contraction. Pulmonary edema, shortness of breath, and disruption in systemic blood pressure are symptoms associated with acute exacerbations of heart failure.

These disease processes often lead to insufficient cardiac output to sustain mild or moderate levels of exercise and proper function of other body organs; progressive worsening eventually results in cardiogenic shock, arrhythmias, electromechanical dissociation, and death. In order to monitor the progression of the disease and to assess efficacy of prescribed treatment, it is desirable to obtain accurate measures of the heart geometry, and the mechanical pumping capability of the heart, under a variety of metabolic conditions. These parameters have typically been measured through the use of external echocardiogram equipment in a clinical setting. However, the measurement procedure is time consuming and expensive to perform for even a resting patient, and cannot be practically performed while replicating a range of metabolic conditions. Typically, the echocardiography procedure is performed infrequently, and months or years may lapse between successive tests, resulting in a poor understanding of the progress of the disease or whether or not intervening therapies have been efficacious. Quite often, only anecdotal evidence from the patient is available to gauge the efficacy of the prescribed treatment.

It has been proposed to employ sensors that respond to mechanical activity of the heart to provide an indication of the strength, velocity or range of motion of one or more of the heart chambers or valves. It is desirable that such information complement information obtained from EGM signals to more confidently detect arrhythmias or trigger delivery of appropriate therapies. It is also desirable to derive indicators of intrinsic cardiac performance and response to delivered therapies that can be employed to confirm or adjust therapy delivery, or to indicate the state and progress of the underlying cardiac disease.

It has been proposed to employ permanently implantable sensors that provide a more direct measure of mechanical motion of muscle mass or particular structures of the heart, including the opening and closing of heart valves and the motion or deformation of the septal wall and the ventricular and atrial walls. Such sensors include intracardiac pressure sensors, accelerometers, impedance measurement electrode systems, and Doppler motion sensors.

As noted in U.S. Pat. No. 5,544,656, measurement of myocardial wall thickness, as well as end-systolic and end-diastolic dimensions, may be useful in evaluating the effects of changes in regional myocardial function and contractility, including evaluating myocardial oxygen supply and demand, in acute and chronic animal studies. A transit-time sonomicrometry system is disclosed in the background of the '656 patent that uses two piezoelectric crystals, one as a transmitter and the other as a receiver, and operates by measuring the time required for ultrasound to travel between the transmitting and receiving transducers. An advantage of this system is its ability to provide an absolute dimension signal output calibrated in units of distance.

The '656 patent also discloses a closed-loop, single-crystal, ultrasonic sonomicrometer capable of identifying the myocardial muscle/blood interface and continuously tracking this interface throughout the cardiac cycle using a piezoelectric transducer that operates in the manner of a Doppler echo sensor implanted at least partly in the myocardium and partly in the blood within a heart chamber.

Sonomicrometer systems that are installed epicardially about the heart to measure heart movement across a number of vectors are also disclosed in the article "Miniature Implantable Sonomicrometer System," by Robert D. Lee et al., (Journal of Applied Physiology, Vol. 28, No. 1, January 1970, pp. 110–112), in EP0 467 695 A2, and in PCT publication WO 00/69490. The Lee article describes an implantable monitoring system attached to the epicardial electrodes. Invasive surgery is necessary to expose locations where sonomicrometer crystals may be surgically attached to the epicardium.

Some of the various chronically implanted sensors described above are intended to be incorporated into lead bodies that are typically introduced transvenously into the relatively low pressure right heart chamber or blood vessels accessible from the right atrium through the patient's venous system. The introduction of such sensors into left heart chambers through the arterial system introduces complications that may be difficult to manage both acutely and chronically. The surgical approach to the exterior of the heart is also not favored as it may complicate the surgery and recovery of the patient. However, measurement of left heart function remains desirable in a number of clinical cases including chronic heart failure.

Stadler et al. (U.S. Pat. No. 6,795,732) discloses a system and method for determining mechanical heart function and measuring mechanical heart performance of both left and right heart chambers without intruding into a left heart chamber or requiring invasive surgery to access the epicardium of the left heart chamber. The system disclosed by Stadler et al. may be incorporated in IMDs (for therapy delivery) and/or implantable monitoring devices employing dimension sensors, such as piezoelectric sonomicrometry crystals. U.S. Pat. No. 6,795,732 to Stadler et al. is assigned to the present assignee and is hereby incorporated by reference in its entirety.

The dimension sensors of Stadler et al. comprise at least a first sonomicrometer piezoelectric crystal mounted to a first lead body implanted into or in relation to one heart chamber, e.g., the right ventricle (RV), that operates as an ultrasound transmitter when a drive signal is applied to it or as an ultrasound receiver, and at least one second sonomicrometer crystal mounted to a second lead body implanted into or in relation to a second heart chamber, e.g., the left ventricle (LV), the left atrium (LA), or the right atrium (RA), that operates as an ultrasound receiver or as an ultrasound transmitter when a drive signal is applied to it, respectively. The ultrasound receiver converts impinging ultrasound energy transmitted from the ultrasound transmitter through blood and heart tissue into an electrical signal. The time delay between the generation of the transmitted ultrasound signal and the reception of the ultrasound wave varies as a function of distance between the ultrasound transmitter and receiver, which in turn varies with contraction and expansion of a heart chamber between the first and second sonomicrometer crystals. One or more additional sonomicrometer piezoelectric crystals can be mounted to additional lead bodies, such that the distances between the three or more sonomicrometer crystals can be determined. In each case, the sonomicrometer crystals are distributed about a heart chamber of interest such that the distance between the separated ultrasound transmitter and receiver crystal pairs changes with contraction and relaxation of the heart chamber.

The RV-LV distance between the RV and LV crystals of Stadler et al. is a measure of LV dimension. Changes in the LV dimension over the cardiac cycle are correlated with changes in LV volume as the LV fills during diastole and empties during systole. The LV-RA distance between the LV and RA crystals varies as a function of RA mechanical activity as the RA fills and empties in a pattern during normal sinus rhythm that markedly differs from the pattern exhibited during atrial fibrillation and other forms of ineffective atrial contraction. The RV-RA distance and RV-LA distance between the RV sonomicrometer crystal and the respective RA and LA sonomicrometer crystals varies as a function of a mixture of atrial and ventricular activity.

Stadler et al. discloses incorporating sonomicrometer piezoelectric crystals into cardiac leads, distributing sonomicrometer piezoelectric crystals about the heart chambers, and incorporating a control and measurement system in the operating system of an IMD that measures the distance between the sonomicrometer crystals as the heart expands and contracts over each heart cycle. First and second cardiac pacing leads or cardioversion/defibrillation leads bearing first and second sonomicrometer crystals, respectively, are implanted through the coronary sinus (CS) and into the great cardiac vein along the LV and in the RV apex, respectively. The lead conductors are coupled to emission, reception, and dimension measurement circuitry within an IMD IPG or monitor that drives one selected piezoelectric crystal as an emitter or generator and the other piezoelectric crystals as receivers, whereby the distances between the crystal pairs can be measured as a function of the measured transit time for the transmitted signal to be received by multiplying the time of travel by the speed of sound in the tissue.

Stadler et al. also discloses incorporating a sonomicrometer crystal into a pacing lead with two or more conductors such that the crystal is wired in parallel with two of the conductors in the lead. For example, a crystal could be wired in parallel with the ring and tip pace/sense electrodes of a pacing lead. The ultrasound crystal has very low impedance to signals near its resonance frequency (near 1 MHz), and very high impedance to lower frequency signals. Pacing pulses, which contain lower frequencies, would preferentially be delivered to the tissue via the tip and ring electrodes, whereas high frequency pulses to excite the ultrasound crystal would be preferentially delivered to the crystal. Additionally, the low pass filter of the pacing sense amplifier does not pass the very high frequency ultrasound signals emitted by the crystals. Thus, the sonomicrometer function does not interfere with normal pacing and sensing functions. As an alternative implementation, the pacing pulse could be delivered simultaneously to the tip and ring pace/sense electrodes, with the IPG case or can as an anode, thereby delivering an effective pacing pulse without any energy dissipation through the ultrasound crystal. As a second alternative, filtering circuitry could be incorporated into the lead to ensure delivery of pacing pulses to the pace/sense electrodes and ultrasound pulses to the crystals.

Pacing therapies delivered by implantable devices may, in some cases, cause asynchronous left ventricular contraction, particularly when pacing the right ventricular apex. In contrast, left ventricular, multi-site, or alternative site right ventricular pacing may lessen the asynchrony of left ventricular contraction (i.e., improve synchrony of left ventricular contractions). The ability of these pacing therapies to resynchronize ventricular contractions may depend on the precise pacing site locations, as well as on pacing parameters such as the programmed AV delay, VV delay interval, and possibly other programmable pacing parameters. However, no clinically accepted method currently exists to reliably evaluate and optimize cardiac performance using sensors in conjunction with an implantable device.

BRIEF SUMMARY OF THE INVENTION

Certain embodiments of the invention provide a method for evaluating and monitoring ventricular performance using indices of ventricular performance derived from cardiac dimension signals obtained from sensors incorporated into permanent pacing leads, temporary guide wires or catheters, or passive transducers surgically placed for such purpose without a catheter.

Certain embodiments of the invention provide a method of operating an IMD to evaluate and monitor ventricular performance using indices of ventricular performance derived from LV dimension measurements, and using the information to optimize ventricular performance by adjusting the operation of the IMD. IMD adjustments may include changing programmed pacing parameters, such as AV delay and V-V delay (in bi-ventricular pacing systems), or by adjusting pacing site location.

Certain embodiments of the invention provide an IMD adapted to evaluate and monitor ventricular performance using indices of ventricular performance derived from LV dimension measurements. The IMD may be adjusted manually, for example by an operator via programmer telemetry commands based on information stored in the IMD, or the adjustment may be automatic, based on an algorithmic response to measured indices of ventricular performance.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

DETAILED DESCRIPTION OF THE ILLUSTRATED EMBODIMENTS

Figure 1:
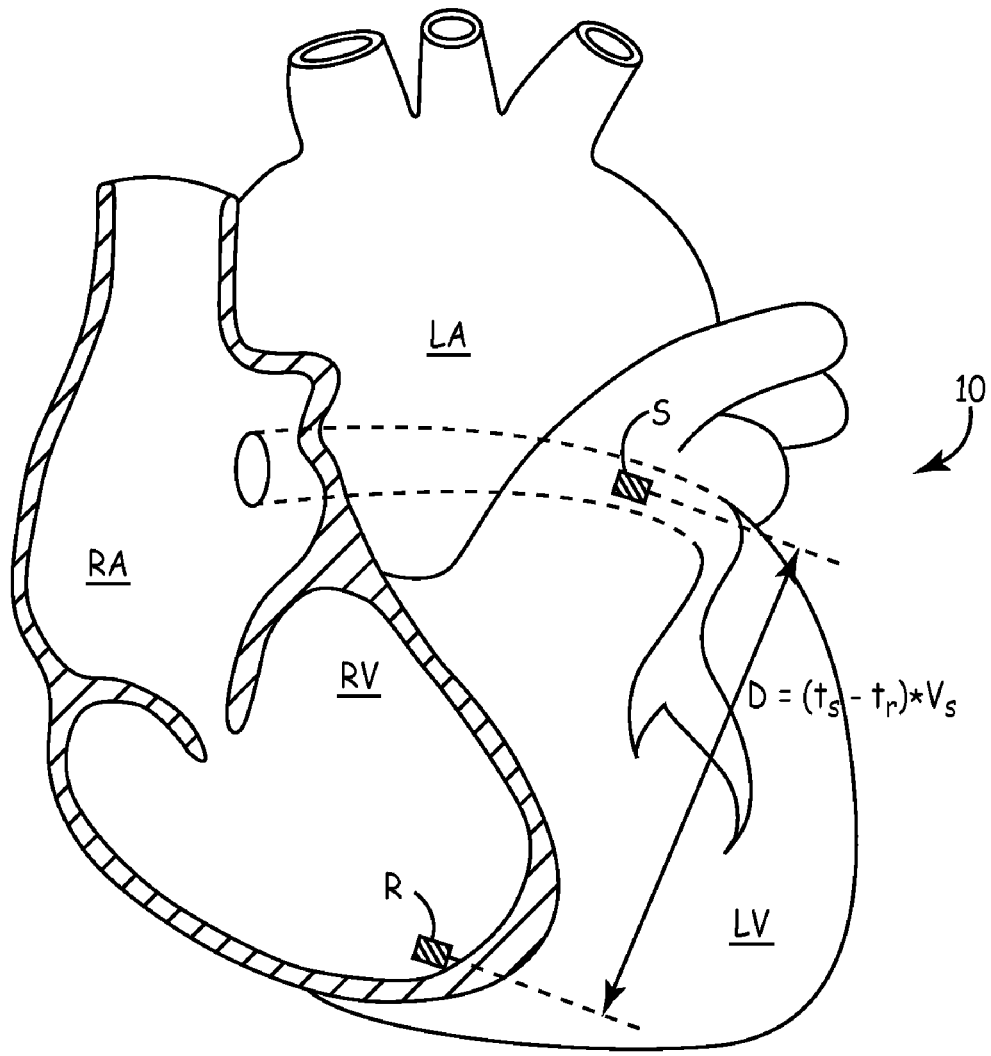
FIG. 1 is a diagram of a heart with sensors positioned to measure left ventricular dimension (LV Dim) in accordance with an embodiment of the invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention.

In the following detailed description, references are made to illustrative embodiments for carrying out the invention. It is understood that other embodiments may be utilized without departing from the scope of the invention. For example, the invention is disclosed in detail herein in the context of an AV sequential, three chamber or four chamber, pacing system operating in demand, atrial tracking, and triggered pacing modes for restoring synchrony in depolarizations and contraction of left and right ventricles in sequence with atrial sensed and paced events for treating heart failure and/or bradycardia in those chambers. This embodiment of the invention is programmable to operate as a three or four chamber pacing system having an AV synchronous operating mode for restoring upper and lower heart chamber synchronization and right and left atrial and/or ventricular chamber depolarization synchrony.

It should be appreciated that the present invention may also be utilized in other embodiments, such as an implantable monitor to gather data in patients suffering from various forms of heart failure. The system of the present invention may also be incorporated into an anti-tachyarrhythmia system including specific high rate pacing and cardioversion shock therapies associated with typical implantable cardioverter defibrillators (ICDs) for providing staged therapies to treat tachyarrhythmias and optionally including bradycardia pacing systems as are known in the art.

It will be therefore understood that the various uses of the dimension signals, and the indices of cardiac performance derived therefrom, can be employed separately or in various combinations in multi-site monitoring, pacing and/or ICD systems and can alternatively be used in simpler dual-chamber and single-chamber pacemakers, monitors and ICDs which may comprise components of the embodiment of the invention illustrated herein.

Embodiments of the invention are therefore not limited to cardiac resynchronization therapy (CRT) devices, and may be employed in many various types of implantable cardiac devices. However, for purposes of illustration only, the invention is described below in the context of a CRT device having bi-ventricular pacing capabilities.

FIG. 1 illustrates the basic sonomicrometry technique disclosed by Stadler et al. for measuring LV Dim as a function of time. As shown, sensors such as piezoelectric sonomicrometer crystals, are placed in two locations that span a portion of the left ventricle. Other types of sensors having the ability to transmit and receive energy may also be used. Acoustic, fibre-optic, infrared, x-ray, RF, and many other forms of electromagnetic energy may be envisioned as having the ability to be employed as a sensor for use in measuring LV Dim. The LV Dim signal is produced by measuring the time delay between sending and receiving energy, and converting the time delay to distance by multiplying by the speed of the signal.

The locations for placement of the sensors may be as shown in FIG. 1, where sensors are placed in the right ventricular apex and the distal coronary sinus using a lead or guide wire or guide catheter. Alternate locations may also be chosen, for example placing sensors on the outside of the heart using epicardial leads such that the two sensors span a portion of the left ventricle, or placing transducers directly on the epicardium or endocardium without a specific pacing lead. Once positioned, the two sensors should remain in fixed locations relative to the heart such that measurements of LV Dim share a common reference and can be compared. However, it is also envisioned that sensors may become dislodged or may be intentionally repositioned at a later time, and that a new reference or baseline LV Dim signal would be generated.

FIG. 1 also illustrates the basic theory that may be used to measure the LV Dim signal using sonomicrometry crystals as the sensors. An electric potential is applied to one of the piezoelectric sonomicrometry crystals (S), creating vibrations and sending sound pulses toward the receiving crystal (R), which generates an electric potential induced by the vibrations. The distance between the crystals (D) is calculated as the time between the signals sent and received $(t_S - t_R)$ multiplied by the velocity of the signal $(V_s)$, or $D = (t_S - t_R) \cdot V_s$.

One embodiment of the invention incorporates the use of sensors positioned on endocardial leads for placement in the heart. This lead-based sonomicrometry (LBS) approach may involve positioning one transducer in the right ventricular (RV) apex and the other in the distal coronary sinus (CS), for example, in order to measure LV Dim, as shown in the system of FIG. 2.

Figure 2:
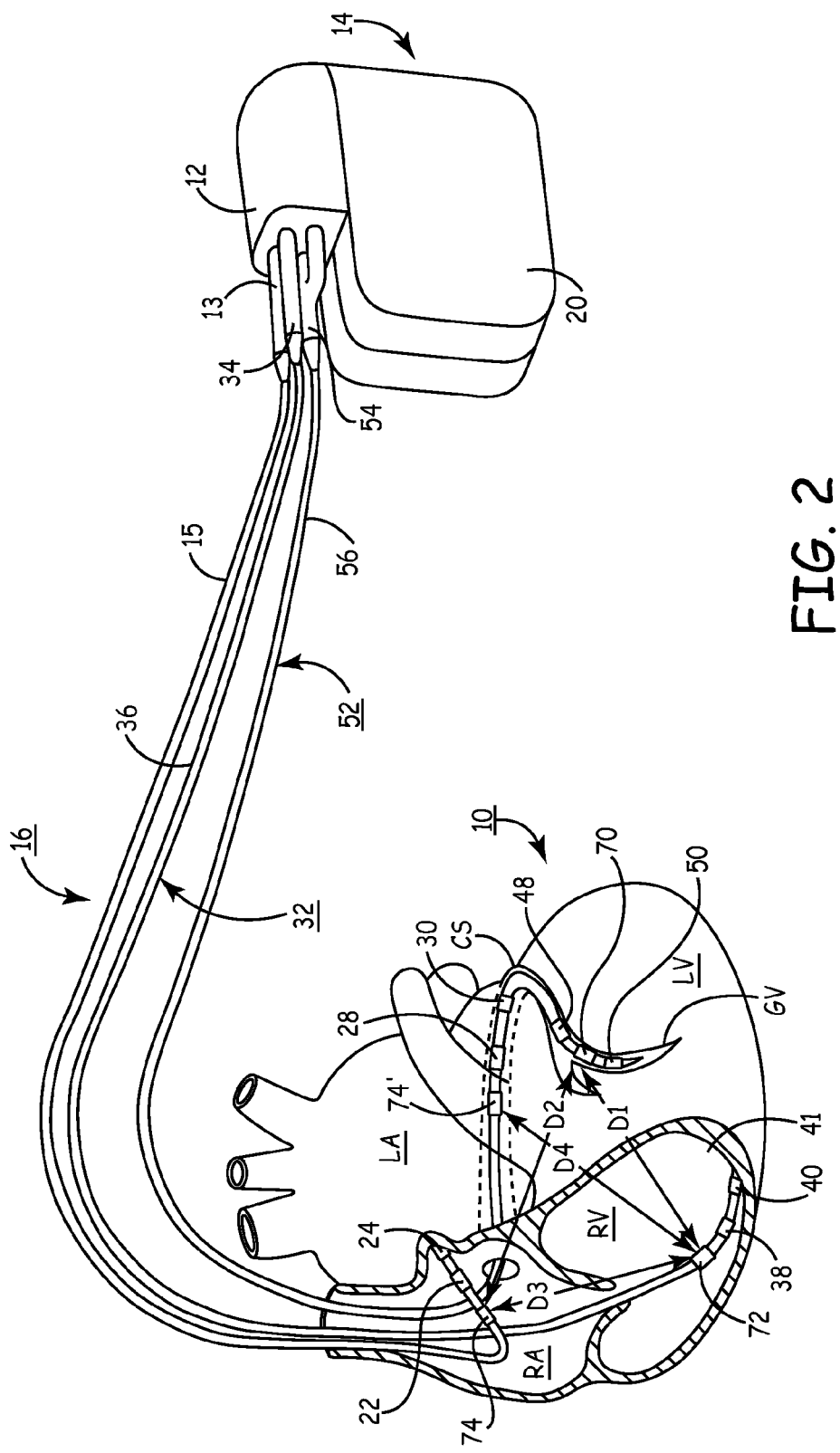
FIG. 2 is a diagram of a heart and an implantable medical device (IMD) coupled to pacing leads and sensors located in the heart according to an embodiment of the invention.

In FIG. 2, heart 10 includes the upper heart chambers, the right atrium (RA) and left atrium (LA), and the lower heart chambers, the right ventricle (RV) and left ventricle (LV), and the various blood vessels attached thereto. The coronary sinus (CS) extends from the opening in the RA laterally around the LA and LV wall to form the great cardiac vein (GV) that extends further inferiorly into branches of the GV. FIG. 2 also shows a schematic representation of an implanted, three or four chamber cardiac pacemaker or monitor or ICD (hereinafter referred to as IPG 14) of the above-noted types for restoring AV sequential contractions of the atrial and ventricular chambers and simultaneous or sequential pacing of the right and left ventricles, and/or for monitoring the mechanical function of one or more heart chambers and/or delivering anti-tachyarrhythmia therapies.

IPG 14 depicted in FIG. 2 is implanted subcutaneously in a patient's body between the skin and the ribs. Three endocardial leads 16, 32 and 52 connect the IPG 14 with the RA, the RV and both the LA and the LV, respectively. Each lead has two electrical conductors and at least one pace/sense electrode, and a remote indifferent can electrode 20 may be formed as part of the outer surface of the housing of the IPG 14. The depicted positions in or about the right and left heart chambers are merely exemplary.

In the embodiment of FIG. 2, RA lead 16 is transvenously passed through the superior vena cava (SVC) and into the RA of the heart 10, and the distal end of the RA lead 16 is attached to the RA wall within the RA appendage by an attachment mechanism 24 that can form one pace/sense electrode. Lead 16 is formed with an in-line connector 13 fitting into IPG connector block 12. The in-line connector 13 is coupled to an RA lead conductor pair within lead body 15 and connected with distal tip RA pace/sense electrode 24 and a proximal ring-shaped RA pace/sense electrode 22. Delivery of RA pace pulses and sensing of RA sense events may be effected between the distal tip RA pace/sense electrode 24 and proximal ring-shaped RA pace/sense electrode 22. Alternatively, a unipolar endocardial RA lead could be substituted for the depicted bipolar endocardial RA lead 16. In an embodiment where IPG 14 comprises an ICD, the RA lead 16 can also include an elongated RA/SVC cardioversion/defibrillation electrode and associated conductor and connector element.

In the embodiment of FIG. 2, RV lead 32 is transvenously advanced through the SVC and the RA and into the RV where its distal tip RV pace/sense electrode 40 is fixed in place in the RV apex by a conventional distal attachment mechanism 41 (which may also constitute the distal tip pace/sense electrode). The RV lead 32 is formed with an RV lead conductor pair within lead body 36 extending from an in-line connector 34 fitting into IPG connector block 12. A first conductor of the RV lead conductor pair is connected with distal tip RV pace/sense electrode 40, and a second conductor of the RV lead conductor pair is connected with the ring-shaped RV pace/sense electrode 38. Delivery of RV pace pulses and sensing of RV sense events may be effected between the distal tip RV pace/sense electrode 40 and the proximal ring-shaped RV pace/sense electrode 38. Alternatively, a unipolar endocardial RV lead could be substituted for the depicted bipolar endocardial RV lead 32. In the ICD embodiment, the RV lead 32 can also include an elongated RV cardioversion/defibrillation electrode and associated conductor and connector element.

A multi-polar, endocardial CS lead 52 is advanced transvenously through the SVC, the RA, the ostium of the CS, the CS itself, and into the GV or a further cardiac vessel branching from the GV. A pair of distal, ring-shaped, LV/CS pace/sense electrodes 48 and 50 are thus located deep in the GV alongside the LV to allow delivery of LV pace pulses and sensing of LV sense events. The LV pacing pulses may be delivered to the LV simultaneously with or in timed relation with the delivery of pacing pulses to the RV. As shown in the illustrated embodiment of FIG. 2, LV/CS lead 52 may also have proximal, ring-shaped, LA/CS pace/sense electrodes 28 and 30 positioned along the CS lead body 56 to lie in the larger diameter CS adjacent the LA.

The LV/CS lead 52 is formed with a multiple conductor lead body 56 coupled at a proximal end connector 54 fitting into IPG connector block 12. In this case, the CS lead body 56 may encase electrically insulated LV and LA lead conductor pairs extending distally from connector elements of a dual bipolar connector 54. A small diameter lead body 56 may be selected in order to place the distal LV/CS pace/sense electrode 50 further distal in a vein branching inferiorly from the GV. In an alternate embodiment, LV/CS lead 52 could bear a single LA/CS pace/sense electrode 28 and/or a single LV/CS pace/sense electrode 50 for unipolar operation. Typically, CS lead 52 does not employ any fixation mechanism and instead relies on the close confinement within these vessels to maintain the pace/sense electrode or electrodes or cardioversion/defibrillation electrode at a desired site. In an embodiment incorporating an ICD, CS lead 52 can also include an elongated CS/LV cardioversion/defibrillation electrode and associated conductor and connector element.

In accordance with one embodiment of the invention, a sensor 70 may be incorporated within a distal segment of the lead body 56 of LV/CS lead 52 to be located alongside the LV, and a sensor 72 may be incorporated within a distal segment of the lead body 36 of RV lead 32. An additional sensor 74 may also be located more proximally on the RA lead body 15 to locate it in the RA or SVC. Additionally or alternatively, a sensor 74' may be incorporated within a more proximal segment of the CS lead body 56 of LV/CS lead 52 to be located alongside the LA.

In one embodiment, sensors 70, 72, and 74 or 74' may comprise sonomicrometer crystals, as previously noted. The sonomicrometer crystals can each be formed as a cylindrical piezoelectric crystal tube sandwiched between an inner tubular electrode and an outer tubular electrode and fitted around the lead body 36 of the type described in U.S. Pat. No. 5,795,298. Various sonomicrometer systems for measuring distance between a piezoelectric crystal acting as a transmitter of ultrasonic energy, and a receiving piezoelectric crystal that vibrates and provides an output signal when exposed to the ultrasonic energy, are disclosed in U.S. Pat. Nos. 5,779,638, 5,795,298, 5,817,022 and 5,830,144.

In the embodiment shown in FIG. 2, the LA lead conductors of LV/CS lead 52 that are connected to the more proximal LA CS pace/sense electrodes 28 and 30 may also be connected to the electrodes of the sonomicrometer crystal 74'. Similarly, the LV lead conductors of LV/CS lead 52 that are connected to the more distal LV CS pace/sense electrodes 50 and 48 may also be connected to the electrodes of the sonomicrometer crystal 70. The RV lead conductors of RV lead 32 that are connected to the RV pace/sense electrodes 40 and 38 may also be connected to the electrodes of the sonomicrometer crystal 72. The RA lead conductors of RA lead 16 that are connected to the RA pace/sense electrodes 24 and 22 may also be connected to the electrodes of the sonomicrometer crystal 74.

An electrode of the piezoelectric crystals 70, 72, 74, and 74' may also be employed as an indifferent pace/sense electrode to provide bipolar pacing and sensing, replacing the indifferent ring-shaped pace/sense electrodes on the same lead body. The piezoelectric crystals 70, 72, 74, and 74' can be located distal to or between pace/sense electrodes or proximal to the pace/sense electrode or electrodes as shown. The particular depicted locations and relative sizes and spacings between pace/sense electrodes and sonomicrometer crystals are not necessarily to scale and are exaggerated for convenience of illustration.

In certain embodiments of the invention, IPG 14 may comprise an ICD and one or more of the leads 16, 32 and 52 may also incorporate cardioversion/defibrillation electrodes and lead conductors extending thereto through the lead bodies for delivering atrial and/or ventricular cardioversion/defibrillation shocks in any of the configurations and operating modes known in the art.

The sonomicrometer crystals 70, 72, 74 and 74' are thereby disposed apart by the RV-LV distance (denoted as D1 in FIG. 2), the LV-RA distance (denoted as D2 in FIG. 2), the RV-RA distance (denoted as D3 in FIG. 2), and the RV-LA distance (denoted as D4 in FIG. 2). The RV-LV distance (D1) between the RV and LV crystals provides a measure of LV dimension (LV Dim), and changes in the LV Dim signal over a cardiac cycle are strongly correlated with changes in LV volume as the LV fills during diastole and empties during systole. Alternately, the RV-LA distance (D2) between the RV and LA crystals may also provide a measure of LV Dim in certain embodiments of the invention, possibly as a back-up to D1, or possibly to augment the information from D1.

Figure 3:
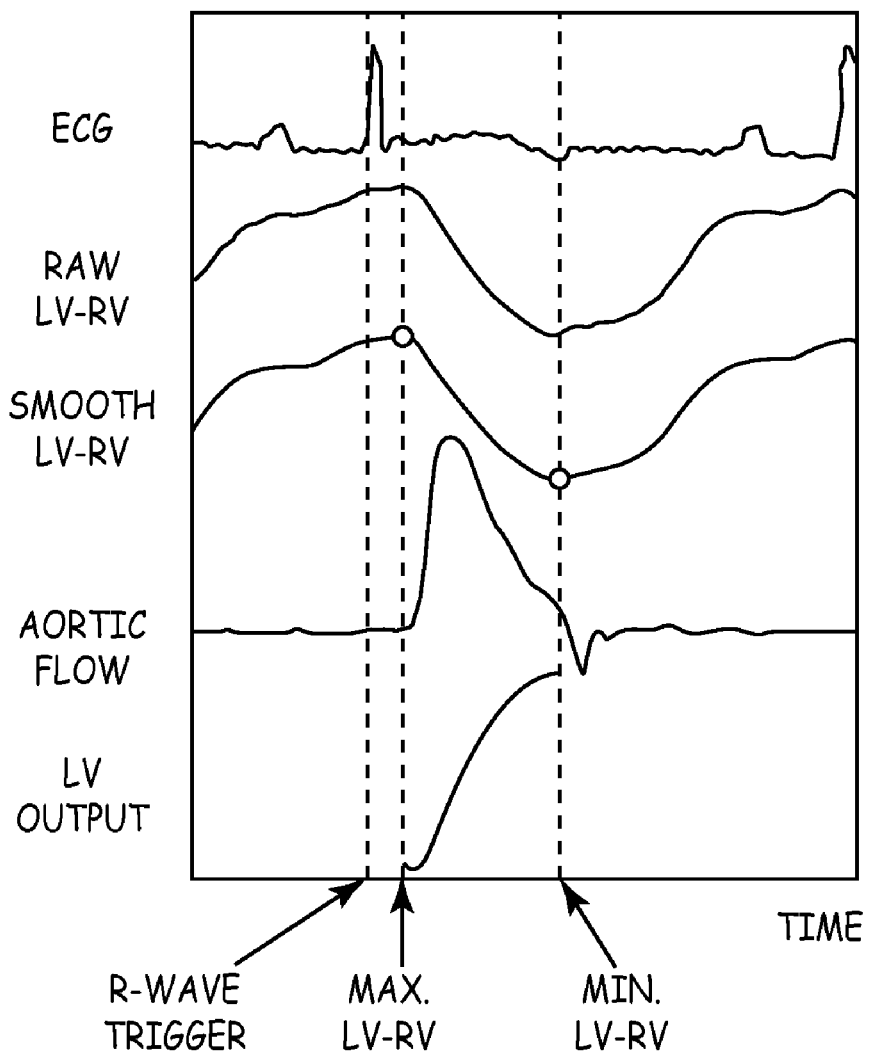
FIG. 3 is a timing diagram showing the relationship between the ECG signal during a cardiac cycle and various mechanical properties associated with heart movement during a cardiac cycle.

FIG. 3 shows the relationship between the LV Dim signal (labeled "LV-RV" in FIG. 3) and an electrocardiogram signal (ECG) for a heart in normal sinus rhythm. The peak of the LV Dim signal occurs at the point labeled "max LV-RV" and identifies the beginning of the systolic function (ejection) of the heart. The point labeled "min LV-RV" identifies the end of the systolic function and the beginning of the diastolic function (filling) of the heart.

Figure 4:
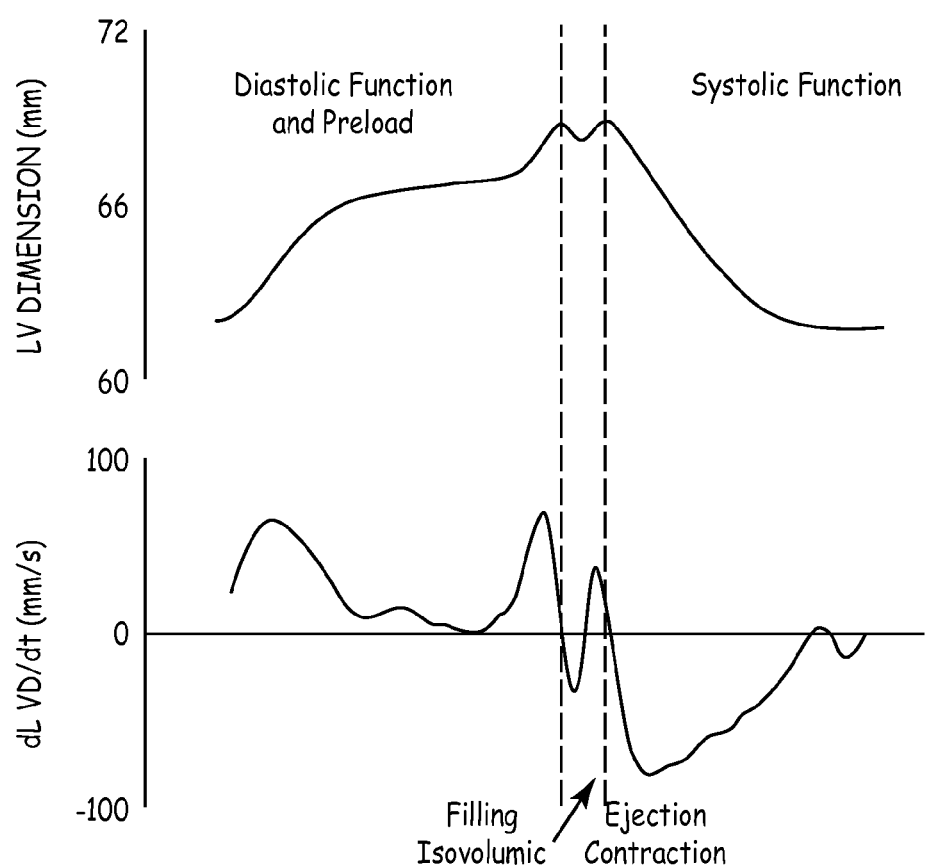
FIG. 4 is a diagram of LV Dim over time and the first derivative of LV Dim with respect to time as measured according to an embodiment of the invention.

FIG. 4 shows an example of the LV Dim signal as a function of time over a cardiac cycle, as well as the first derivative of LV Dim with respect to time. The LV Dim signal shown in FIG. 4 spans a single cardiac cycle, comprising a ventricular filling phase and a ventricular ejection phase. The transition from the filling phase to the ejection phase is also indicated in FIG. 4. In addition to information about systolic function (ejection), diastolic function (filling), and extent of filling (preload), this signal may also contain information about the synchrony or effectiveness of LV contraction during the isovolumic contraction phase. The isovolumic contraction phase is identified in FIG. 4 as the time period between the two vertical dashed lines. This phase begins with closure of the mitral valve (first dashed line) and ends with opening of the aortic valve (second dashed line), and is characterized by a sudden increase in left ventricular pressure (not shown in FIG. 4).

The shape of the LV Dim signal is correlated with changes in LV volume over a cardiac cycle, while the shape of the first derivative of the LV Dim signal (labeled "dLVD/dt") is analogous to mitral valve flow during ventricular filling and inverse aortic flow during ejection. Thus, the LV Dim signal and its derivative contain important information about cardiac performance, including diastolic function, systolic function and synchrony of ventricular contractions.

Figure 5:
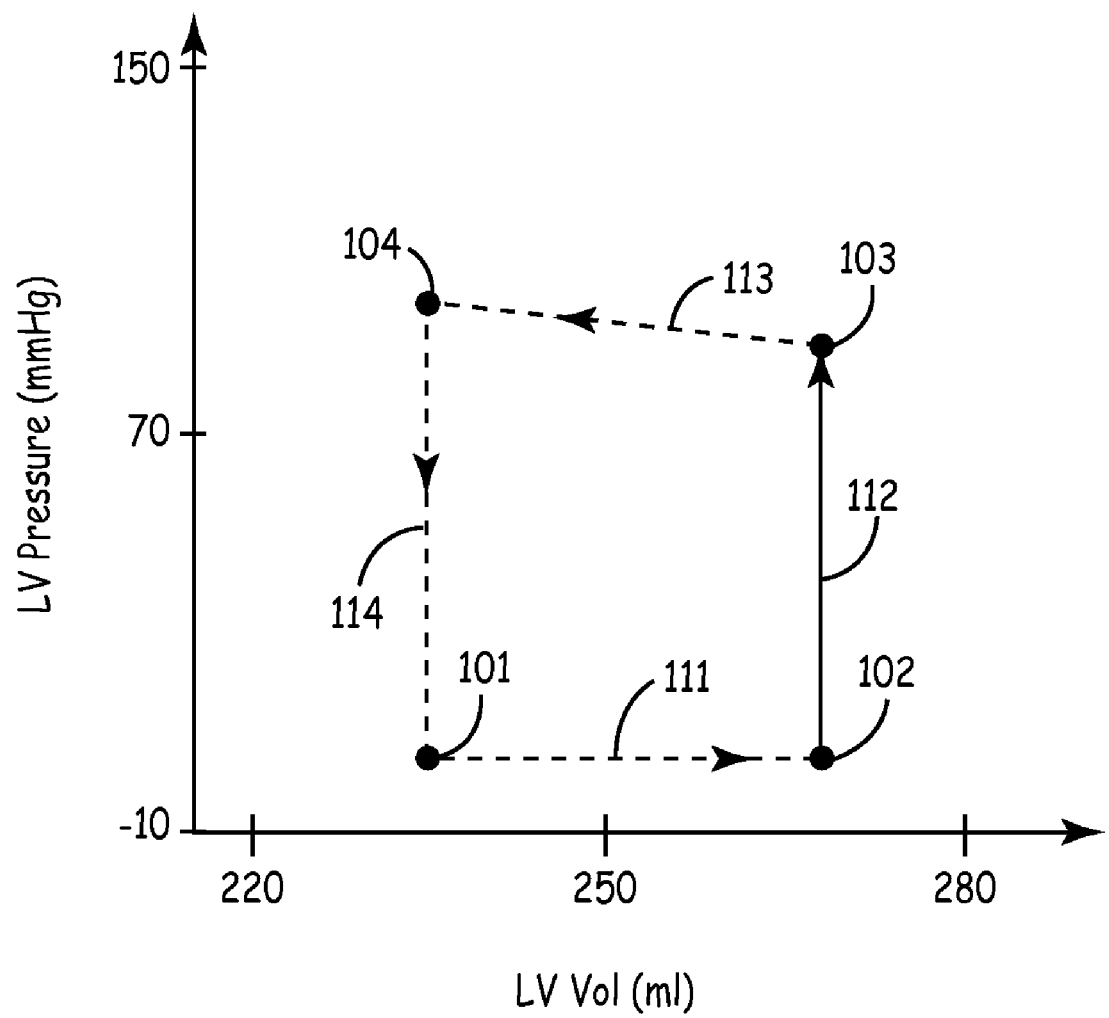
FIG. 5 is a plot of LV Pressure vs. LV Volume for a normal heart over a cardiac cycle.

As noted above, "isovolumic contraction" occurs during the transition between ventricular filling and ejection, and is characterized by a sharp increase in pressure within the ventricle due to the contraction of the ventricle following closure of the mitral valve and prior to opening of the aortic valve. The isovolumic contraction phase of a normal cardiac cycle may be illustrated on a pressure vs. volume plot and is shown as the solid vertical line in FIG. 5, which displays LV pressure versus LV volume over a cardiac cycle. A cardiac cycle follows the somewhat rectangular path shown in FIG. 5. The point labeled 101 corresponds to the opening of the mitral valve, which allows blood to begin flowing into the LV. As blood continues to flow into the LV, the LV expands in volume, corresponding to line segment 111, which represents ventricular filling. At 102, the mitral valve closes, ending the filling phase and beginning the isovolumic contraction phase. Between mitral valve closure 102 and aortic valve opening 103, the LV begins to contract, but due to the near incompressibility of liquids (i.e., blood), LV pressure rises sharply during isovolumic contraction, as indicated by segment 112. From aortic valve opening 103 to aortic valve closure 104, blood is rapidly ejected at high pressure from the LV to the aorta (line segment 113). The end of the ventricular contraction and the closure of the aortic valve causes LV pressure to rapidly decrease until the mitral valve again opens at 101 to begin another cardiac cycle.

Figure 6:
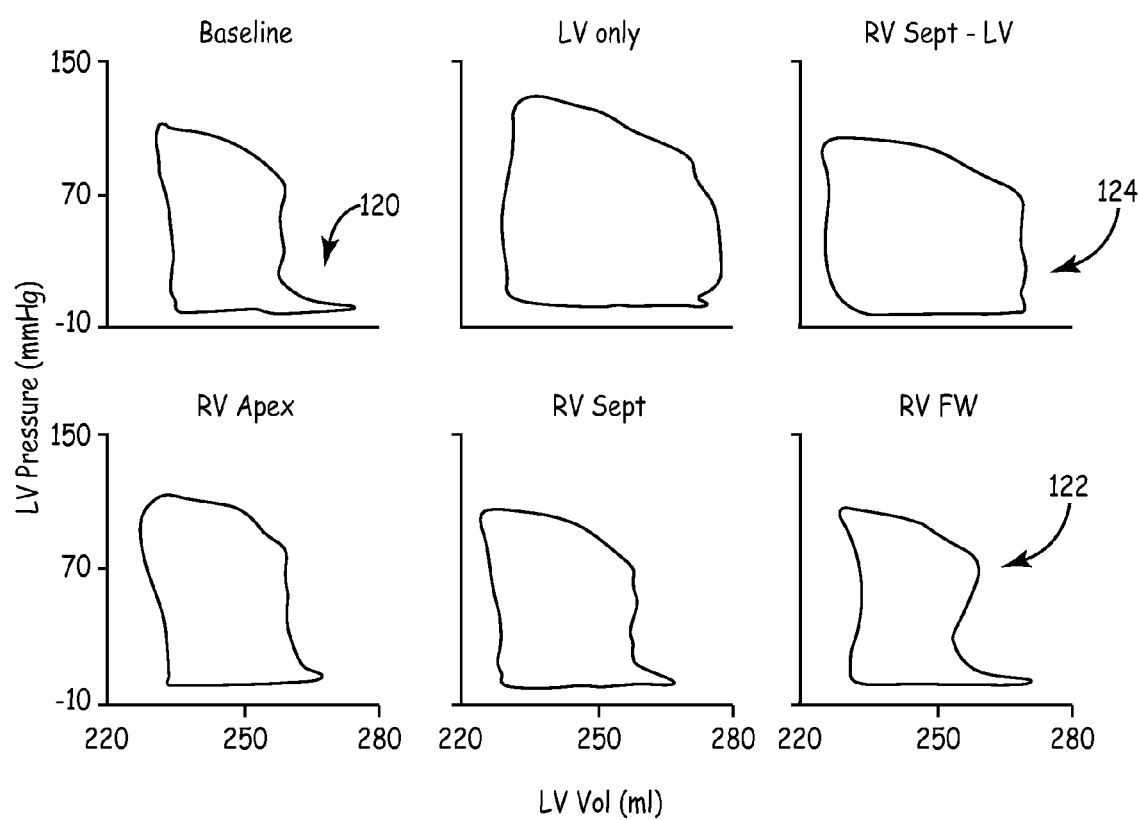
FIG. 6 is a plot of LV Pressure vs. LV Volume over a cardiac cycle for a number of different pacing site locations/configurations.

FIG. 6 shows examples of cardiac cycles for a number of different pacing lead locations. The isovolumic contraction phase of several of these plots reveal shape changes that are indicative of a reduction in ventricular performance. For example, 120 shows a decrease in the LV volume at the beginning of isovolumic contraction, indicating possible LV asynchrony for this lead configuration. 124 indicates that for this particular lead configuration (bi-ventricular pacing at the RV septal wall and in the LV), a relatively straight/vertical isovolumic contraction has occurred, possibly showing that ventricular synchrony has been improved or restored, which should result in improved hemodynamics for the patient.

Asynchronous contraction of the left ventricle may lead to mitral valve regurgitation and/or isovolumic shape changes of the LV. Either of these effects may be detected upon observation of changes in LV volume, either real or apparent. For example, mitral valve regurgitation may result in an actual decrease in LV Volume, whereas a shape change of the LV may cause measured LV Volume to change without an actual decrease in LV Volume. Since the LV Dim signal is highly correlated to LV volume, ventricular performance may be evaluated by analysis of certain features of the LV Dim signal that may be manifestations of either mitral valve regurgitation or isovolumic shape changes of the LV.

Figure 7:
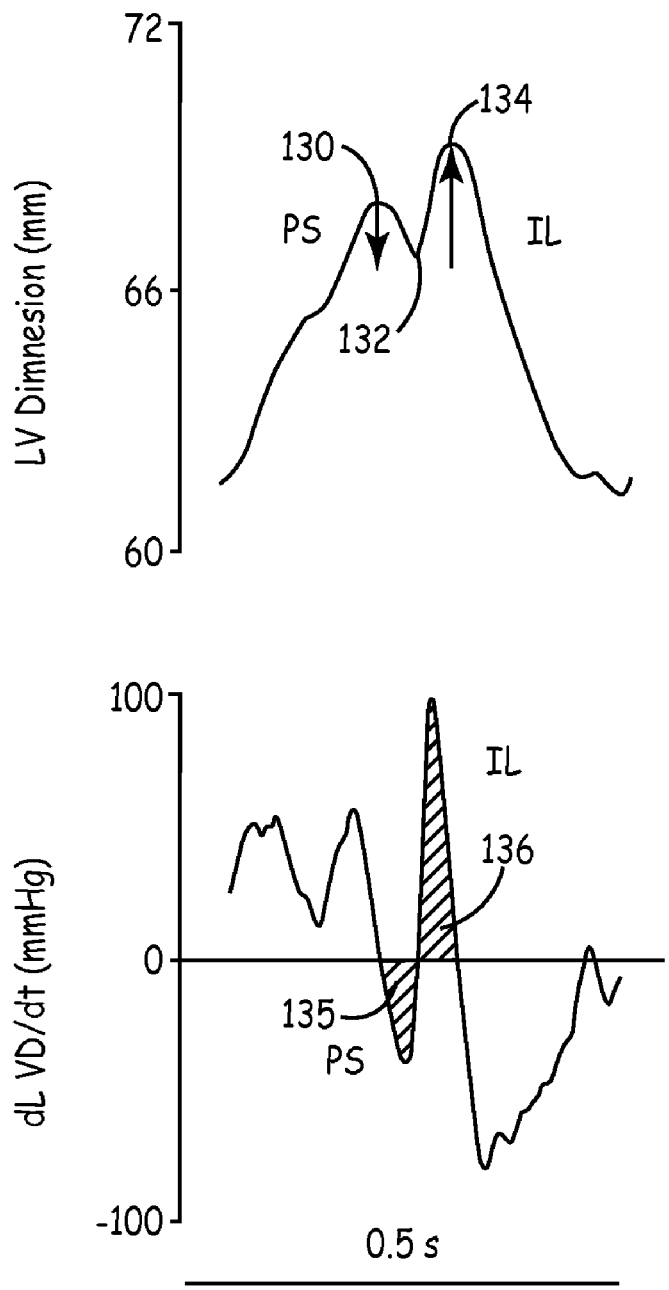
FIG. 7 is an enlarged view of LV Dim, illustrating the measurement of two indices of cardiac performance in accordance with an embodiment of the invention.

Measurement of the LV Dim signal as a function of time, using means such as lead-based sonomicrometry (LBS), permits calculation of two novel indices of ventricular performance. FIG. 7 is an enlarged drawing of a portion of the signals shown in FIG. 4. The LV Dim signal in FIG. 7 illustrates the measurement of two indices of ventricular performance, "premature shortening" (PS) and "isovolumic lengthening" (IL). PS and IL are quantitative indices of ventricular performance that can be derived and measured from the LV Dim signal as described below.

Premature shortening (PS) is defined as the decrease in LV Dim from a first local maximum 130 near end-diastole associated with mitral valve closure to a local (relative) minimum or inflection point 132. PS is shown in FIG. 7 as the decrease in LV Dim from the first peak 130 to the "dip" 132 in the LV Dim signal. Isovolumic lengthening (IL) is defined as the increase in left ventricular dimension from the local (relative) minimum 132 to a second local maximum 134 at or near the time of aortic valve opening. IL is shown in FIG. 7 as the increase in LV Dim from the "dip" 132 to the second peak 134 in the LV Dim signal. In a normal, synchronous LV contraction, both PS and IL would have values at or near zero.

One of ordinary skill in the art will appreciate that measurement of PS and IL may be accomplished by equivalent mathematical means. For example, the derivative of the LV Dim signal may be mathematically integrated over the period of time corresponding to PS or IL to determine the same numerical values. A mathematical integration may, for example, calculate the area of the shaded regions 135, 136, yielding values that correspond to or are equivalent to the measured values of PS and IL, respectively, determined directly from the LV Dim signal. Such equivalent mathematical techniques of measuring the values of PS and IL are contemplated and are understood to fall within the scope of the invention.

Figure 8:
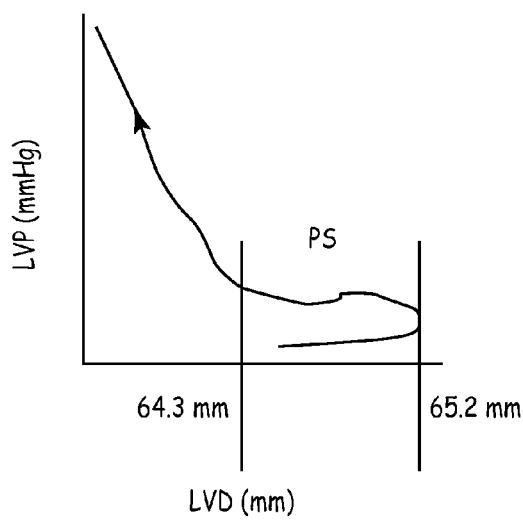
FIG. 8 is an enlarged plot of LV Pressure vs. LV Dim, showing the corresponding shape change associated with Premature Shortening (PS) in accordance with an embodiment of the invention.
Figure 8A:
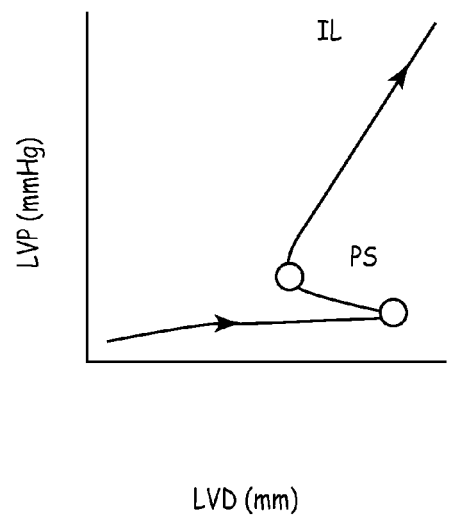
FIG. 8a is an enlarged plot of LV Pressure vs. LV Dim, showing the corresponding shape change associated with Premature Shortening (PS) and Isovolumic Lengthening (IL) in accordance with an embodiment of the invention.

Referring again to FIG. 6, it was noted that the isovolumic contraction portion of the curve may provide information regarding ventricular performance, including the presence of LV asynchrony. The relationship between the pressure-volume curves of FIG. 6 and the PS and IL values determined from a corresponding LV Dim measurement discussed above is described in FIGS. 8 and 8(a), where portions of the isovolumic contraction segment of representative LV pressure-dimension curves have been enlarged. In the example of FIG. 8, a decrease in LV dimension occurs during isovolumic contraction, corresponding to the premature shortening (PS) of the LV. In the example of FIG. 8(a), a decrease followed by an increase in the LV dimension during isovolumic contraction is shown, corresponding to both the PS and IL of the LV Dim signal, respectively. Thus, the LV Dim signal contains some of the same information about ventricular performance that can be obtained by measuring LV pressure and LV volume over a cardiac cycle, but is amenable to a simpler lead-based measurement, such as by lead-based sonomicrometry (LBS). Further, the measurement of LV Dim may be accomplished by a chronically implanted lead-based system, with PS and IL measurements calculated and stored by an IMD, or used in an algorithm by an IMD to attempt to optimize ventricular performance, either automatically (on a periodic, on-going basis, for example), or by an operator using external equipment to communicate with an IMD, for example to re-program pacing parameters based on stored values of PS and IL retrieved from the IMD.

Figure 9:
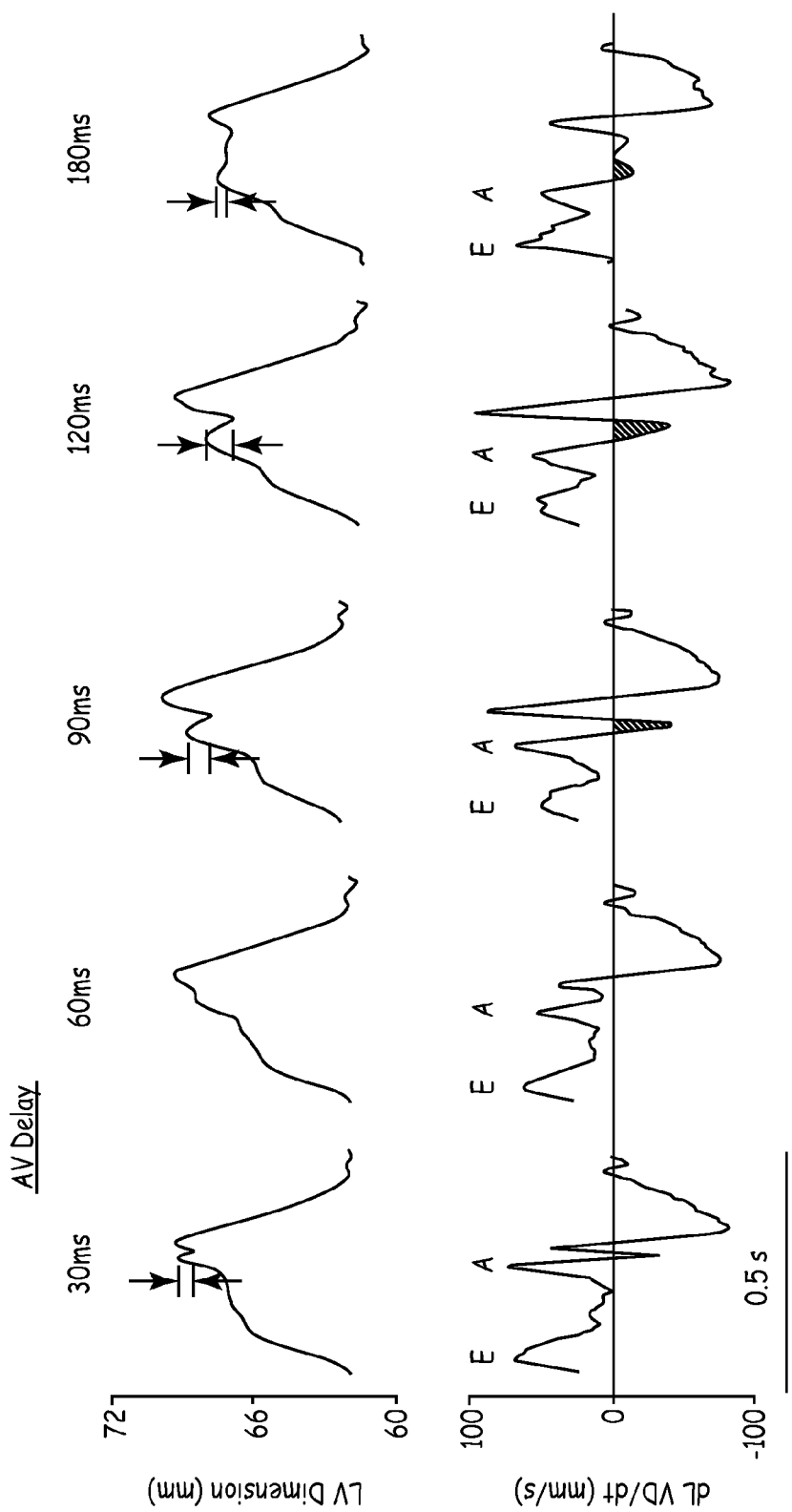
FIG. 9 is a series of plots of LV Dim showing the effect of varying the paced AV Delay on the measured value of PS according to an embodiment of the invention.
Figure 10:
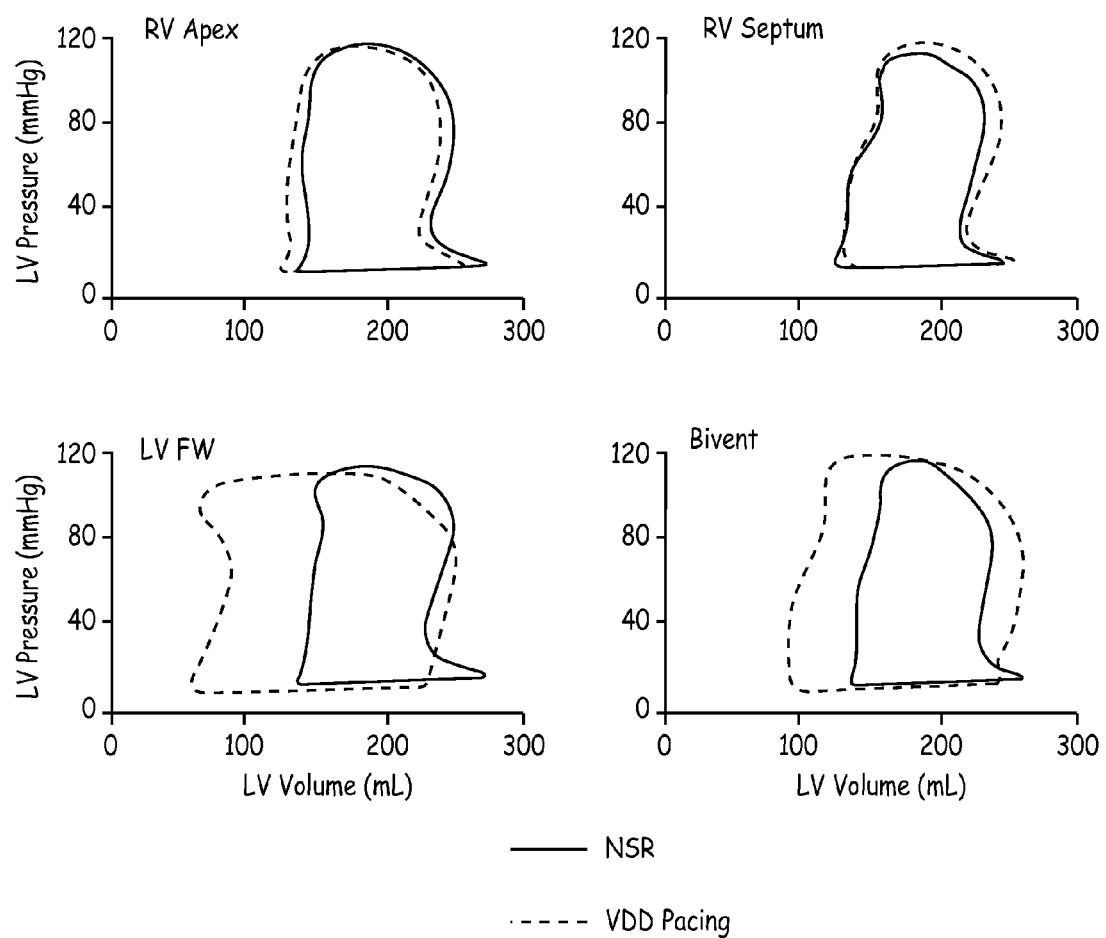
FIG. 10 is a plot of LV Pressure vs. LV Volume over a cardiac cycle for a number of different pacing site locations and pacing mode configurations.

Changes in the values of PS and IL (and hence in ventricular performance) may be associated with variations in the programmed atrio-ventricular (AV) delay in a paced heart, as well as with variations in the location of ventricular pacing leads, as shown in FIGS. 9 and 10, respectively. Variations in inter-ventricular pacing delay (V—V) between the left and right ventricles may also affect synchrony in bi-ventricularly paced hearts. By using PS and IL to optimize the location of pacing sites and to adjust the AV and V—V delays, ventricular performance may be optimized and the heart may provide improved cardiac output. Hence, measuring PS and IL may provide the ability to optimize ventricular performance both at the time of implantation of a pacing system, as well as post-implant, either automatically or manually using PS and IL data.

Figure 11:
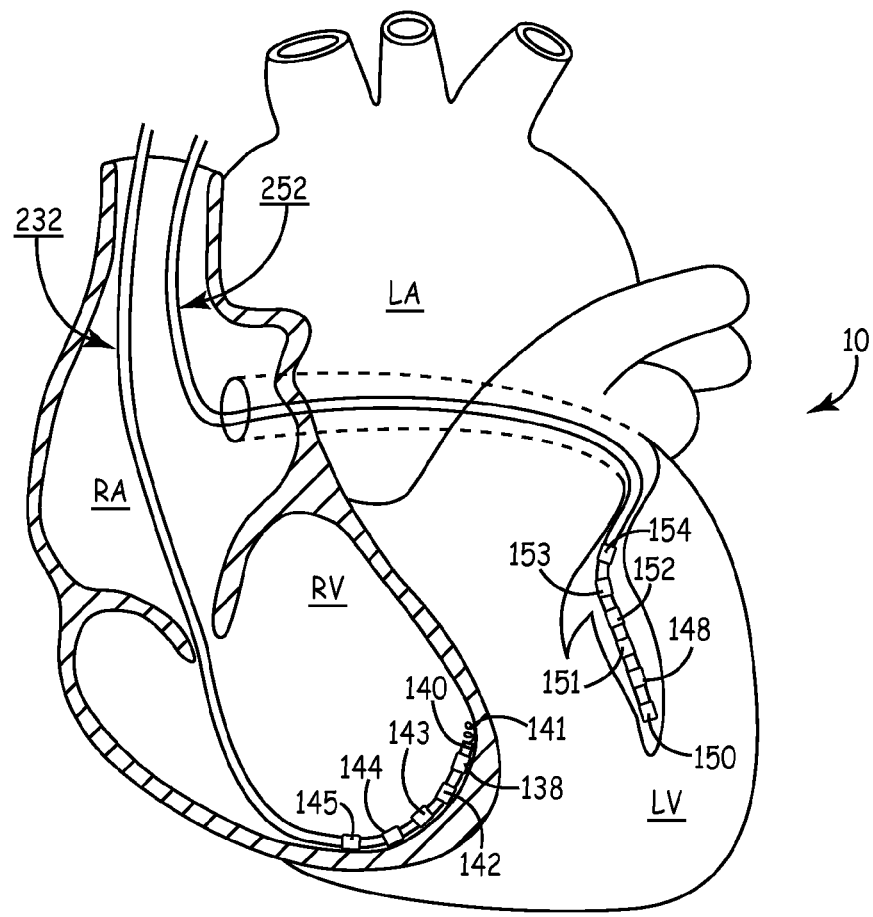
FIG. 11 is a diagram of a heart with multi-site pacing leads implanted according to an embodiment of the invention.

In one possible embodiment of the invention, multi-site pacing leads may be employed in conjunction with an IMD pacing system. Multi-site pacing leads, as are known in the art, provide the ability to vary the pacing site in a chronically implanted lead. FIG. 11 shows an embodiment of the invention that incorporates multi-site pacing leads for RV lead 232 and the LV/CS lead 252. For example, RV lead 232 has the ability to pace and/or sense from any pair of electrodes 141, 140, 138, 142, 143, 144, and 145. To change the pacing site location, for example, an operator may be able to select the pacing site between the fixation tip electrode 141 and ring electrode 140 in order to select the RV septal wall as one of the pacing site locations. An operator may make measurements of PS and IL with the RV septal wall as the pacing site location, for example, then select a new pacing site location, such as between ring electrodes 142 and 143, to evaluate the impact or change on measured values of PS and IL. Similarly, the LV/CS lead 252 may have the ability to pace from multiple sites. For example, pacing and sensing may be selected to occur between ring electrodes 148 and 150 for an initial measurement of PS and IL, for comparison with PS and IL measurements made using an alternate pacing site location, such as between ring electrodes 153 and 154.

Another embodiment of the invention comprises an IMD with the ability to automatically vary the pacing site locations in either or both the RV lead 232 and the LV/CS lead 252 in order to attempt to minimize the measured values of PS and/or IL, and to thereby improve ventricular performance. Thus, an embodiment of the invention includes the ability to vary the pacing site location(s) in response to measured values of PS and IL to attempt to improve ventricular performance.

Figure 12:
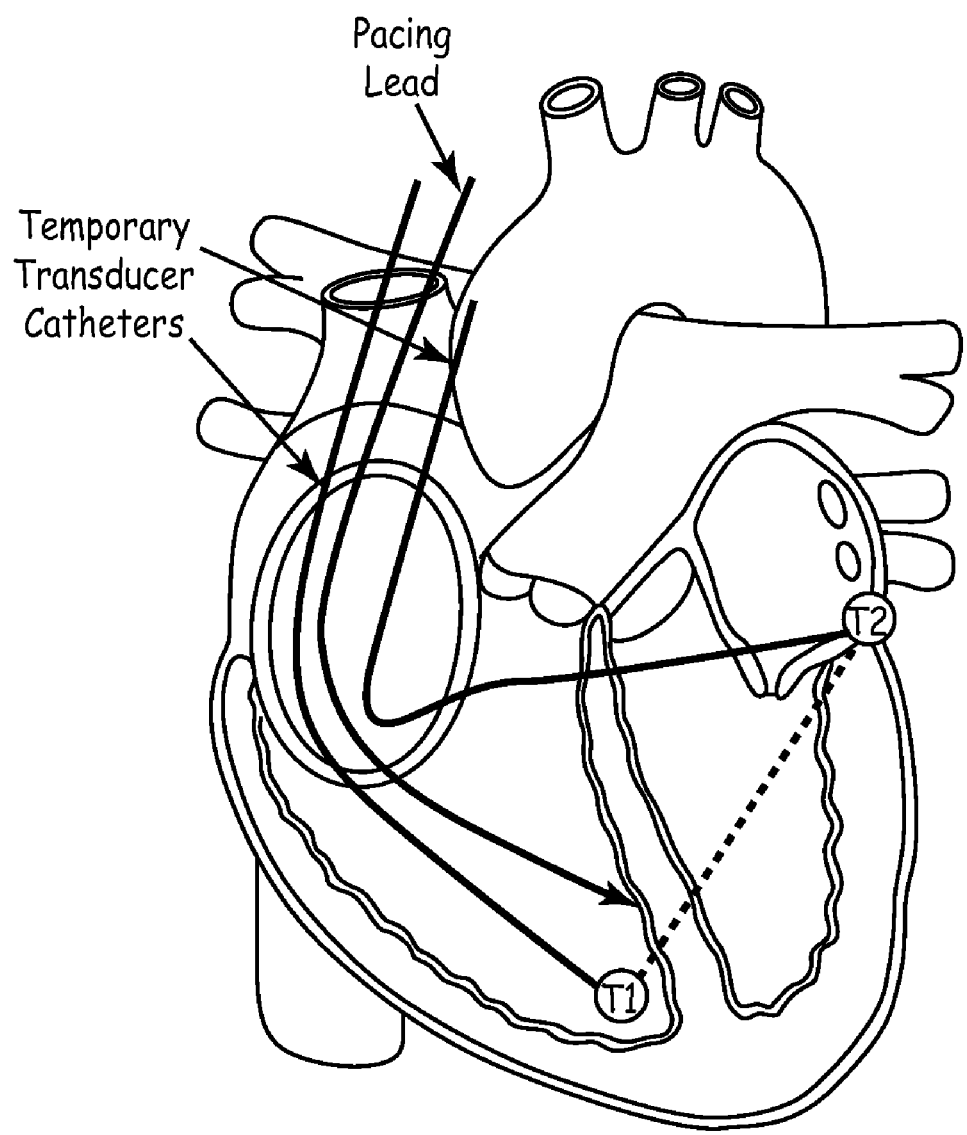
FIG. 12 is a diagram of a heart showing a method of positioning a RV pacing lead using information from temporary sensors according to an embodiment of the invention.
Figure 13:
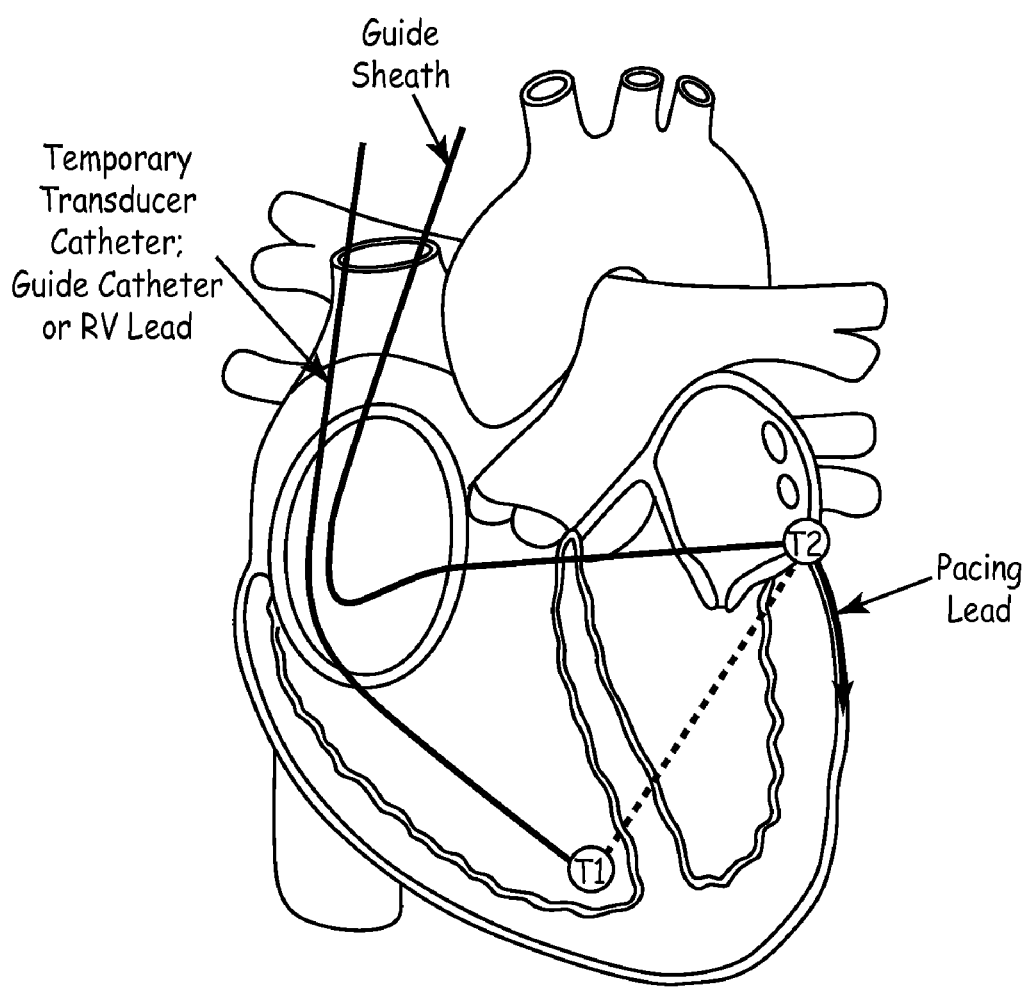
FIG. 13 is a diagram of a heart showing a method of positioning a LV pacing lead using information from temporary sensors according to an embodiment of the invention.

In an alternate embodiment of the invention, sensors 70, 72, 74, and 74' may be placed on temporary catheters or guide wires, for example, to evaluate ventricular performance during lead placement and to determine optimum lead locations to maximize ventricular performance by attempting to minimize the measured values of PS and IL. FIGS. 12 and 13 show this technique being employed for an RV lead and an LV lead, respectively. FIG. 12 shows the use of temporary transducer catheters for measuring values of PS and IL at the time of implantation of an RV lead. As shown in FIG. 12, the temporary transducer catheters may be used to position sensors at the points labeled T1 and T2. The RV lead may then be repeatedly repositioned, measuring PS and IL values at each pacing site location. In this manner, a pacing site location for the RV lead may be chosen that achieves values of PS and/or IL that optimize ventricular performance. Upon finding an optimal pacing site location and affixing the RV lead, the temporary transducer catheters may be removed from the patient's heart.

FIG. 13 shows a similar arrangement for placing a LV lead. Temporary transducer catheters may be employed as described above to position sensors at locations T1 and T2. Alternately, a guide sheath may be used as shown in FIG. 13 to both position a sensor in the coronary sinus, and allow movement of the LV/CS pacing lead longitudinally relative to the guide sheath, for example. Upon determination of a suitable pacing site location for the LV/CS lead, the guide sheath of this embodiment may be removed from the patient's heart. The LV lead, for example, may be slidably guided within a lumen in the guide sheath, as shown in FIG. 13. The guide sheath may include a sensor, such as a piezoelectric sonomicrometry crystal, attached to the guide sheath and held in a relatively stable position within the CS to allow measurements of LV Dim, PS, and IL for different locations of the pace/sense electrode(s) of the LV lead.

Acute measurements of PS and IL, such as provided by temporary transducer catheters with sensors affixed thereto, have the potential benefit of resulting in a system with fewer chronically implanted components. The acute measurements of PS and IL, and the related measurements made at time of implant regarding changes in PS and IL as a function of varying pacing parameters, may comprise sufficient information for the long-term management of an IMD without the need for further measurements of PS and IL. This may result in an IMD system that is easier to monitor and follow-up. Alternately, sensors implanted chronically for continuing measurements of PS and IL during the chronic operation of an IMD may prove to be beneficial in monitoring and evaluating the long-term progress of the patient's heart condition. For example, anecdotal evidence may suggest that "remodeling" of the heart may occur over time due to the improved hemodynamics provided by optimizing ventricular performance. Such remodeling may allow for a series of on-going, future adjustments to further improve ventricular performance, for example. Thus, a clinician/physician may decide that the benefit of having the ability to monitor and evaluate ventricular performance chronically using an IMD may outweigh any added complexity associated with the sensors and lead system necessary to provide this information.

Figure 14:
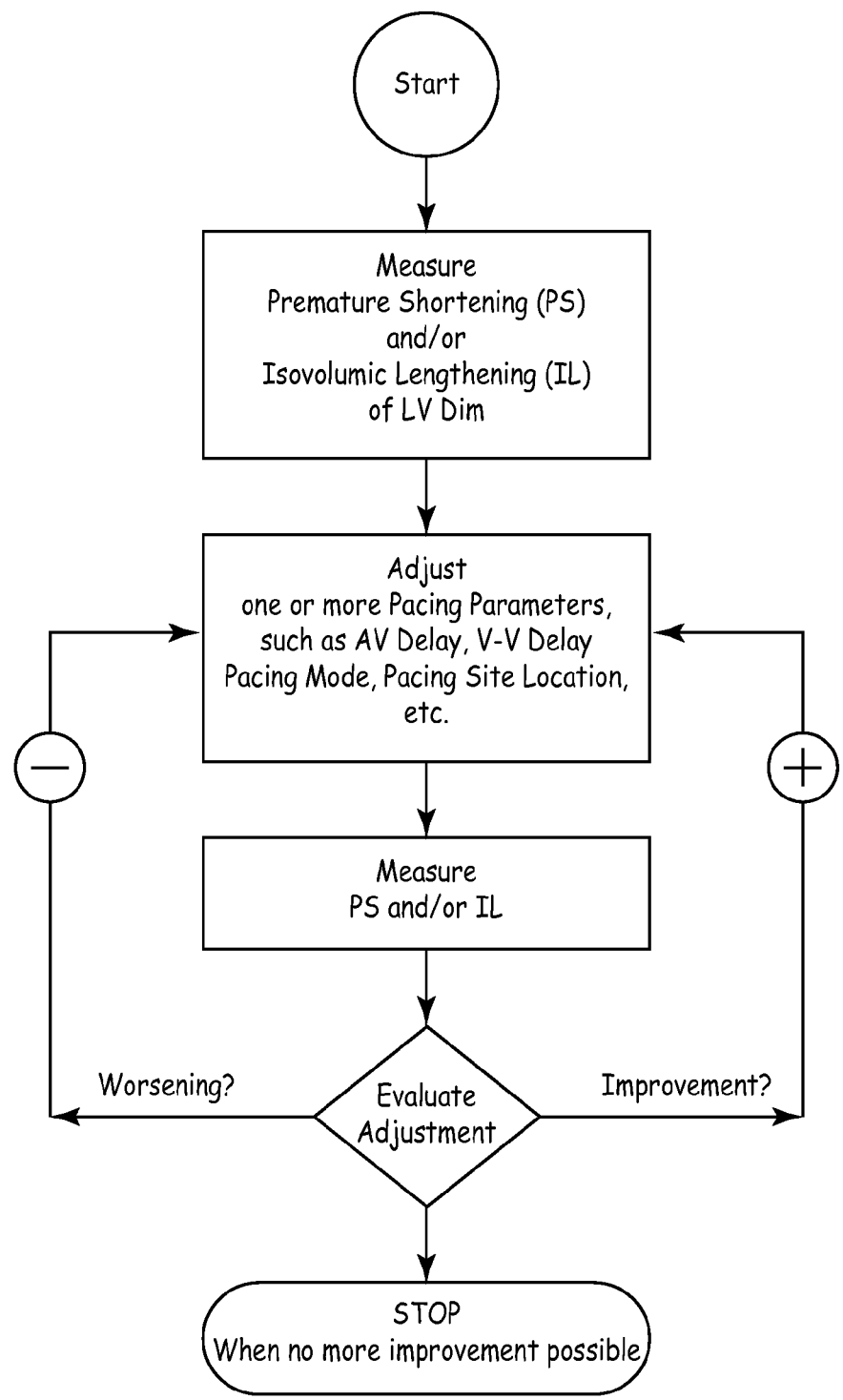
FIG. 14 is a block diagram of a method for automatically adjusting pacing parameters in an IMD according to an embodiment of the invention.

FIG. 14 shows a block diagram of a method for operating an IMD to optimize ventricular performance. The first step in the method is to measure PS and/or IL based on measuring LV Dim over one or more cardiac cycles. An optional step (not shown) may be to derive a criterion from the measured values of PS and/or IL. Such a criterion may be selected by an operator, and may consist of the value of PS by itself, IL by itself, or some weighted function of both PS and IL, for example a weighted average of the two indices. The next step is to adjust a pacing parameter, such as the AV delay, VV delay, pacing mode, pacing rate, pacing site location, etc., possibly based on the measured values of PS and/or IL, or on the criterion derived therefrom. The next step in the method is to measure PS and/or IL after the adjustment in pacing parameter, to (optionally) derive a new criterion from the measured values of PS and/or IL, and determine if there has been an improvement or a worsening in the PS, IL, or criterion values. The last step in the method is to continue adjusting one or more of the pacing parameters until the criterion has been improved to an optimal level, or until no further improvement is possible, then ending the adjustment.

Figure 15:
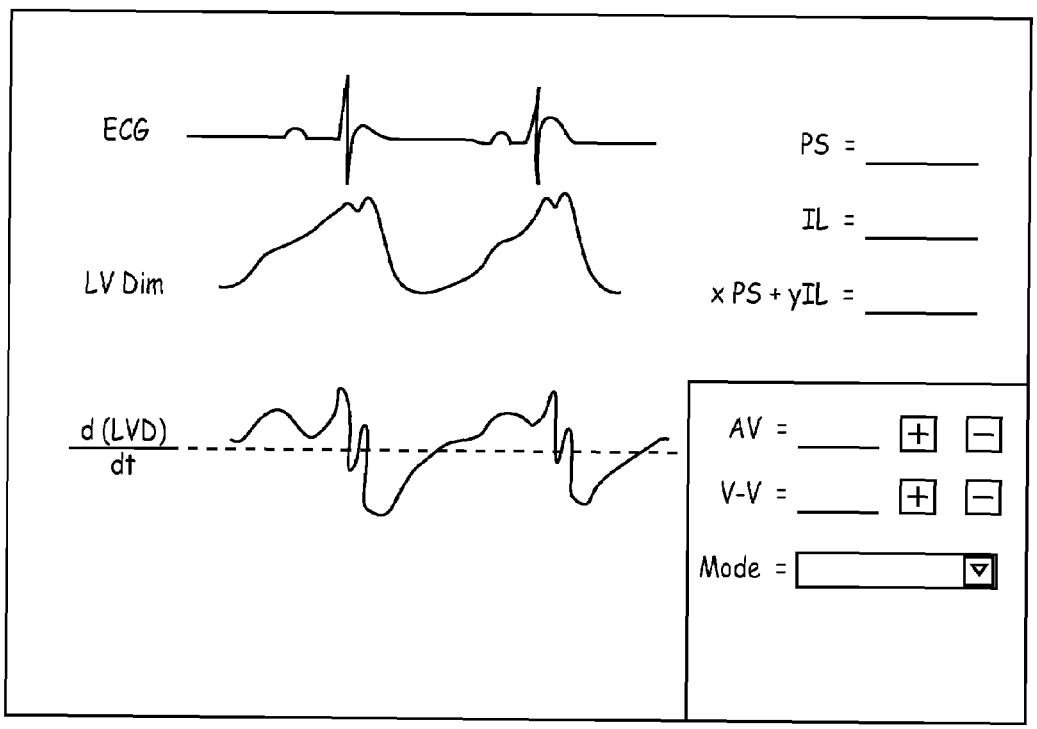
FIG. 15 is a diagram of an exemplary programmer screen for monitoring cardiac performance and manually adjusting pacing parameters according to an embodiment of the invention.

FIG. 15 illustrates an example of a screen shot from a programming device designed to communicate with the IMD via RF telemetry, for example, according to a possible embodiment of the invention. The screen shot in FIG. 15 provides an operator with a real time display of the ECG, LV Dim, and d(LVD)/dt signals, with constantly updating measured values for PS, IL and any criterion of ventricular performance or synchrony determined from the measured values of PS and IL. Furthermore, the programmer's screen may have user-operated buttons, such as touch screen controls, that allow for changes to paced programming parameters (such as AV Delay, V—V Delay, etc.), while watching a real time update in the values of PS, IL, and any ventricular performance criterion. The programmer interface of FIG. 15 would allow an operator to attempt to optimize ventricular performance, both at the time of implant and post-implant, such as at a patient follow-up visit. At the time of implant, for example, the LV Dim signal and its first derivative may be provided by either an acute/temporary sensor system, or by a sensor configuration that is incorporated into the pacing leads. For post-implant use, the IMD could rely on sensor signals from a chronically implanted sensor system, such as those illustrated in FIG. 1, obviating the need for an invasive procedure to place sensors.

The screen shot of FIG. 15 provides a programmer interface that allows an operator (physician, etc.) to interact with an appropriately equipped IMD (i.e., via RF telemetry, for example) and lead system to measure PS and IL, determine a criterion of ventricular performance therefrom, and make adjustments to pacing parameters and/or pacing site locations in order to achieve a "best" criterion value for the particular heart/patient and thereby maximize ventricular performance for the patient.

Thus, embodiments of a METHOD AND APPARATUS FOR EVALUATING VENTRICULAR PERFORMANCE DURING ISOVOLUMIC CONTRACTION are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of evaluating the ventricular performance of a heart comprising:
    positioning a first sensor at a first location of the heart, and a second sensor at a second location of the heart, the first and second locations spanning a portion of a ventricle;
    measuring a distance between the first and second sensors over a cardiac cycle of the heart to produce a ventricular dimension signal as a function of time, the cardiac cycle comprising a ventricular filling phase and a ventricular ejection phase;
    measuring at least one of the following values:
    a) premature shortening (PS) of the ventricular dimension signal,
    the value of PS being equal to the decrease in the ventricular dimension signal
    from a first local maximum value that occurs at or near an end of the ventricular filling phase of the cardiac cycle, to a relative minimum value or inflection point that occurs during a transition from the ventricular filling phase to the ventricular ejection phase of the cardiac cycle; and
    b) isovolumic lengthening (IL) of the ventricular dimension signal,
    the value of IL being equal to the increase in the ventricular dimension signal from the relative minimum value or inflection point that occurs during the transition from the ventricular filling phase to the ventricular ejection phase of the cardiac cycle, to a second local maximum value that occurs at or near a beginning of the ventricular ejection phase of the cardiac cycle; and
    comparing the at least one measured value of PS or IL with at least one reference value or at least one previously measured value of PS or IL.

2. The method of claim 1 wherein a decrease in the at least one measured value of PS or IL with respect to the at least one reference value or the at least one previously measured value of PS or IL generally indicates an improvement in the ventricular performance of the heart.

3. The method of claim 2 wherein a value of approximately zero for PS and IL indicates an optimum level of ventricular performance of the heart.

4. The method of claim 2 wherein a decrease in a sum of the measured values of PS and IL indicates an improvement in the ventricular performance of the heart.

5. The method of claim 1 wherein the first and second sensors are sonomicrometry crystals.

6. The method of claim 5 wherein the sonomicrometry crystals use the piezoelectric effect to transmit and receive sound energy.

7. The method of claim 1 wherein an electromagnetic energy signal is emitted from one of the first and second sensors that causes the other of the first and second sensors to sense the electromagnetic energy signal a time delay later, and wherein the distance between the first and second sensors is a function of the time delay between the emitted and sensed electromagnetic energy signal.

8. The method of claim 1 wherein one of the first and second sensors is positioned generally near a right ventricular apex of the heart, and wherein the other of the first and second sensors is positioned in or near the coronary sinus of the heart.

9. The method of claim 1 further comprising measuring the value of at least one of PS and IL over a plurality of cardiac cycles and determining a weighted average value of at least one of PS and IL for comparison to at least one reference value or at least one previously measured value of PS or IL.

10. The method of claim 1 further comprising:
    determining the value of the first local maximum, the relative minimum, and the second local maximum of the ventricular dimension signal by a method that includes identifying when a first derivative of the ventricular dimension signal changes polarity.

11. The method of claim 1 further comprising:
    determining the value of the first local maximum, the relative minimum, and the second local maximum of the ventricular dimension signal by a method that includes correlation of the ventricular dimension signal with zero crossings of a first derivative of the ventricular dimension signal.

12. The method of claim 1 wherein the heart is operatively coupled to an Implantable Medical Device (IMD) comprising a plurality of leads and device circuitry, the method further comprising:
    storing measured values of at least one of PS and IL in the IMD for comparison to at least one reference value or at least one other measured value of PS or IL to monitor and evaluate changes in the ventricular performance of a heart.

13. The method of claim 12 further comprising:
adjusting the operation of the IMD in response to the measured values of at least one of PS and IL to attempt to reduce subsequent measured values and thereby improve the ventricular performance of a heart.

14. The method of claim 13 wherein the IMD stimulates one or a combination of the right atrium, right ventricle, and left ventricle, the method further comprising
adjusting a pacing parameter to attempt to reduce at least one of PS and IL and thereby improve the ventricular performance of a heart.

15. The method of claim 14 wherein the pacing parameter adjusted is the atrio-ventricular (AV) delay.

16. The method of claim 14 wherein the pacing parameter adjusted is the inter-ventricular (VV) delay.

17. The method of claim 13 wherein the IMD includes the ability to pace from multiple pacing site locations on at least one pacing lead, the method further comprising:
adjusting the pacing site location to attempt to reduce at least one of PS and IL and thereby improve the ventricular performance of a heart.

18. The method of claim 1 wherein the heart is operatively coupled to at least one pacing lead, the method further comprising:
storing measured values of at least one of PS and IL at a given configuration of lead locations;
repositioning the at least one pacing lead;
storing measured values of at least one of PS and IL at a second and subsequent configurations of lead locations; and
adjusting the placement of pacing leads to minimize the measured values and thereby optimize the ventricular performance of a heart.

19. A method of operating an implantable medical device having a plurality of leads and having an implantable medical device circuit enclosed within a hermetically sealed housing, the method comprising:
implanting a first lead bearing a first sonomicrometer crystal at a first location of the heart;
implanting a second lead bearing a second sonomicrometer crystal at a second location of the heart, the first and second locations spanning a portion of the left ventricle;
coupling the first and second leads to the implantable medical device circuit and implanting the housing in a patient; and
operating the implantable medical device by:
during one or more heart cycles, periodically energizing one of the first and second sonomicrometer crystals to emit an ultrasonic frequency emitted signal that causes the other of the first and second sonomicrometer crystals to develop an ultrasonic frequency sense signal;
determining the distance between the first and second sonomicrometer crystals as a function of the time delay between emission of the emitted signal and sensing of the respective sense signal;
measuring at least one of the following values:
a) premature shortening (PS) of the ventricular dimension signal,
the value of PS being equal to the decrease in the ventricular dimension signal from a first local maximum value that occurs at or near an end of the ventricular filling phase of the cardiac cycle, to a relative minimum value or inflection point that occurs during a transition from the ventricular filling phase to the ventricular ejection phase of the cardiac cycle; and
b) isovolumic lengthening (IL) of the ventricular dimension signal,
the value of IL being equal to the increase in the ventricular dimension signal from the relative minimum value or inflection point that occurs during the transition from the ventricular filling phase to the ventricular ejection phase of the cardiac cycle, to a second local maximum value that occurs at or near a beginning of the ventricular ejection phase of the cardiac cycle;
comparing the at least one measured value of PS or IL with at least one reference value or at least one other measured value of PS or IL; and
adjusting the operation of the implantable medical device.

20. An implantable medical device (IMD) for evaluating ventricular performance of a heart comprising:
a plurality of leads and an implantable medical device circuit enclosed within a hermetically sealed housing;
a first lead bearing a first sonomicrometer crystal adapted to be positioned at a first location of the heart;
a second lead bearing a second sonomicrometer crystal adapted to be positioned at a second location of the heart, the first and second locations spanning a portion of the left ventricle, the first and second leads adapted to be coupled to the IMD circuit, the housing of the IMD adapted to be implanted in a patient, and the IMD capable of:
periodically energizing one of the first and second sonomicrometer crystals during one or more heart cycles to emit an ultrasonic frequency emitted signal that causes the other of the first and second sonomicrometer crystals to develop an ultrasonic frequency sense signal;
determining the distance between the first and second sonomicrometer crystals as a function of the time delay between emission of the emitted signal and sensing of the respective sense signal;
measuring at least one of the following values:
a) premature shortening (PS) of the ventricular dimension signal,
the value of PS being equal to the decrease in the ventricular dimension signal from a first local maximum value that occurs at or near an end of the ventricular filling phase of the cardiac cycle, to a relative minimum value or inflection point that occurs during a transition from the ventricular filling phase to the ventricular ejection phase of the cardiac cycle; and
b) isovolumic lengthening (IL) of the ventricular dimension signal,
the value of IL being equal to the increase in the ventricular dimension signal from the relative minimum value or inflection point that occurs during the transition from the ventricular filling phase to the ventricular ejection phase of the cardiac cycle, to a second local maximum value that occurs at or near a beginning of the ventricular ejection phase of the cardiac cycle;
comparing the at least one measured value of PS or IL with at least one reference value or at least one other measured value of PS or IL; and
adjusting the operation of the implantable medical device.

* * * * *